(12) United States Patent
Ishisaka (10) Patent No.: US 7,397,059 B2
(45) Date of Patent: Jul. 8, 2008

(54) RADIATION IMAGE READING SYSTEM

(75) Inventor: Akira Ishisaka, Hachioji (JP)

(73) Assignee: Konica Minolta Medical & Graphic, Inc. (JP)

( * ) Notice: Subject to any disclaimer, the term of this patent is extended or adjusted under 35 U.S.C. 154(b) by 219 days.

(21) Appl. No.: 11/143,509

(22) Filed: Jun. 1, 2005

(65) Prior Publication Data

US 2005/0274917 A1    Dec. 15, 2005

(30) Foreign Application Priority Data

Jun. 9, 2004    (JP) .............................. 2004-171282

(51) Int. Cl.
*G11B 7/135* (2006.01)
*G01T 1/105* (2006.01)

(52) U.S. Cl. ...................... 250/586; 250/584
(58) Field of Classification Search ................. 250/584, 250/586
See application file for complete search history.

(56) References Cited

U.S. PATENT DOCUMENTS 5,841,833 A * 11/1998 Mazess et al. ............. 378/98.9
6,507,025 B1 * 1/2003 Verbinski et al. .......... 250/358.1
2003/0085352 A1 * 5/2003 Lezec et al. ................ 250/306
2005/0220265 A1 * 10/2005 Besson ........................ 378/16

* cited by examiner

*Primary Examiner*—David P. Porta
*Assistant Examiner*—Carolyn Igyarto
(74) *Attorney, Agent, or Firm*—Squire, Sanders & Dempsey L.L.P.

(57) ABSTRACT

The present invention is directed to a radiation image reading system. The system includes a radiation source for irradiating a radiation toward a subject. The radiation source has a size "D". A radiation detector in which large number of detecting devices for detecting the radiation transmitted through the subject are arranged in an array form, for generating an image signal of the subject by detecting the radiation transmitted through the subject by each of the detecting devices. An aperture of each of the detecting devices has a size "A". Also included is a sampling section for sampling the image signal. The size A of the aperture fulfills a condition of $B \leq A \leq 2B$. B is a size of a penumbra on the radiation detector. The size B of the penumbra is represented by $B = D \times (R2/R1)$, where R1 is a distance from the radiation source to the subject and R2 is a distance from the subject to the radiation detector.

3 Claims, 10 Drawing Sheets

ORIGINAL IMAGE SIGNAL g(x)

FIG.4B

SIGNAL AFTER SAMPLING

RADIATION IMAGE READING SYSTEM

BACKGROUND OF THE INVENTION

1. Field of the Invention

The present invention relates to a system for reading a radiation image from an image signal of a subject. In particular, the present invention relates to a sampling technology of an image signal.

2. Description of Related Art

So far, a radiation image such as an X-ray image or the like has been widely used in a medical field for diagnosing a medical condition. In particular, a radiation image according to the Intensifying screen-Film system still remains being used in a world-wide medical field as an imaging system having both a high reliability and an excellent cost performance, as a result of efforts for enhancing a sensitivity and an image quality in a long history. On the other hand, these days, a Computed Radiography (CR) using a photostimulable phosphor sheet is in commercialization and a sensitivity thereof and an image quality thereof have been enhanced. Furthermore, a Flat Panel Detector (FPD) has also been introduced. Therefore, nowadays there are more choices of a system instead of the conventional Intensifying screen-Film system.

Meanwhile, in conjunction with developments of a radiation detector such as a CR, an FPD or the like, opportunities of generating a magnified image for looking at a more detailed structure of the subject are increasing (for example, see JP-Tokukai-2001-311701A and JP-Tokukai-2003-180670A). In the magnified image generation, while it is possible to look at a detailed structure of the subject as mentioned, there is in general a problem of an image deterioration because blur is generated on a subject image according to an image generation condition, since a radiation source is not an ideal point source. In the arts disclosed in JP-Tokukai-2001-311701A and JP-Tokukai-2003-180670A, such a problem is solved by using a phase contrast or the like, and thereby it is possible to obtain a radiation image having an excellent sharpness.

By the way, regardless of a type of the radiation detector such as a CR, an FPD or the like, it is always necessary to have a step of "sampling" in order to obtain a digital signal from an image signal (analog signal) obtained by the radiation detector. According to a known sampling principle, a phenomenon called "aliasing" occurs unless the image signal obtained by the radiation detector is sampled by a sampling frequency being larger than a frequency two times as much as the frequency of the image signal prior to the sampling. When "aliasing" occurs, a false image is generated or a noise is increased.

When a CR is applied as the radiation detector, it is possible to obtain an image signal by following a time series along with a scanning direction of a stimulating light. Therefore, it is possible to prevent the aliasing from occurring in the scanning direction by providing a low pass filter called an anti-aliasing filter. However, since it is not possible to provide such a filter in a sub-scanning direction, which is perpendicular to the scanning direction of the stimulating light, it is not possible to avoid the occurrence of the aliasing in the sub-scanning direction.

On the contrary, when an FPD is applied as the radiation detector, principally or due to a structural reason, it is difficult to place the anti-aliasing filter, and therefore the aliasing always occurs. Further, in this case, the larger a value of a Modulation Transfer Function (MTF) of the detector for obtaining a radiation image having a high sharpness is set, the larger influence the aliasing provides.

Under such circumstances, when an image signal is sampled, it is necessary to perform an optimal sampling corresponding to a type of the radiation detector while the occurrence of the aliasing is considered. Moreover, since it is considered that opportunities of the above-mentioned magnified image generation keep increasing, it is also necessary to perform an optimal sampling in view of the above-mentioned magnified image generation.

SUMMARY OF THE INVENTION

An object of the present invention is to prevent an aliasing from occurring upon a magnified image generation.

In accordance with a first aspect of the present invention, a radiation image reading system comprises: a radiation source for irradiating a radiation toward a subject; a radiation detector for generating an image signal of the subject according to a raster scan technique by detecting the radiation transmitted through the subject; and a sampling section for sampling the image signal so as to make a Nyquist frequency approximately equal to a frequency of a zero point of a penumbra.

According to the system of the first aspect, the sampling section samples an image signal so as to make a Nyquist frequency approximately equal to a frequency of a zero point in a frequency response of a penumbra. Therefore, it is possible to use a frequency response of the penumbra as an anti-aliasing filter in a cross scanning direction, which is perpendicular to a raster scan direction. Consequently, it is possible to prevent the aliasing in the cross scanning direction in a magnified radiography.

In accordance with a second aspect of the present invention, a radiation image reading system comprises: a radiation source for irradiating a radiation toward a subject; a radiation detector in which large number of detecting devices for detecting the radiation transmitted through the subject are arranged in an array form, for generating an image signal of the subject by detecting the radiation transmitted through the subject by each of the detecting devices; and a sampling section for sampling the image signal so as to satisfy a condition of $B \leq A \leq 2B$, where A is a size of a aperture of each of the detecting elements and B is a size of a penumbra on the radiation detector.

According to the system of the second aspect, the sampling section samples an image signal so as to satisfy a condition of $B \leq A \leq 2B$. Thereby, a minus part of a frequency response of an aperture is offset by a frequency response of a penumbra. Consequently, it is possible to prevent the aliasing from occurring in a magnified radiography.

BRIEF DESCRIPTION OF THE DRAWINGS

The present invention will become more fully understood from the detailed description given hereinafter and the accompanying drawing given by way of illustration only, and thus are not intended as a definition of the limits of the present invention, and wherein.

PREFERRED EMBODIMENTS OF THE INVENTION

Hereinafter, a best mode for implementing the present invention will be described with reference to drawings. However, the scope of the invention is not limited to the represented descriptions.

First Embodiment

First, a structure of a radiation image reading system relating to the first embodiment will be briefly described.

Figure 1:
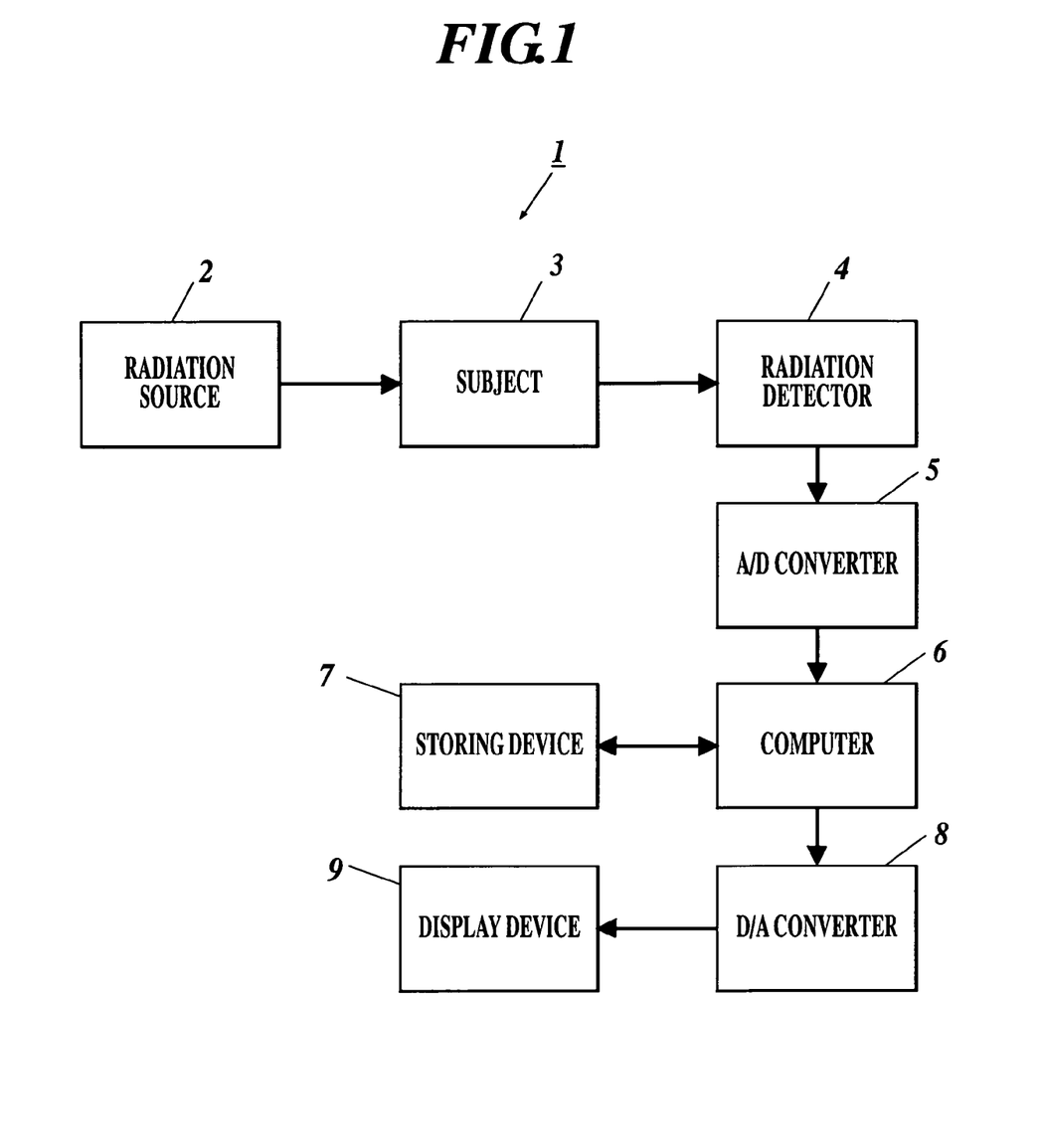
FIG. 1 is a block diagram showing a rough structure of a radiation image reading system.

As shown in FIG. 1, the radiation image reading system 1 comprises a radiation source 2 for irradiating a radiation toward a subject 3, and a radiation detector 4 for detecting the radiation transmitted through the subject 3, for reading a radiation image of the subject 3 based on a detection result of the radiation detector 4.

The radiation detector 4 detects the radiation transmitted through the subject 3 and generates an image signal corresponding to dose of the transmitted radiation as an analog signal. To the radiation detector 4, a generally-known computer 6 is connected through an A/D converter (analog-to-digital converter) 6. In the radiation image reading system 1, the image signal (analog signal) generated by the radiation detector 4 is converted into the digital signal by the A/D converter 5, and the digital signal after the conversion is inputted to the computer 6.

To the computer 6, a generally-known storing device 7 such as a HD (Hard Disc) or the like is connected, and a generally-known display device 9 such as a CRT (Cathode Ray Tube) or the like is connected through a generally-known D/A converter (digital-to-analog converter) 8. In the radiation image reading system 1, the digital signal inputted to the computer 6 is stored in the storing device 7 as digital data, or is converted into an analog signal by the D/A converter 8 to be displayed on the display device 9 as a radiation image of the subject 3.

Figure 2:
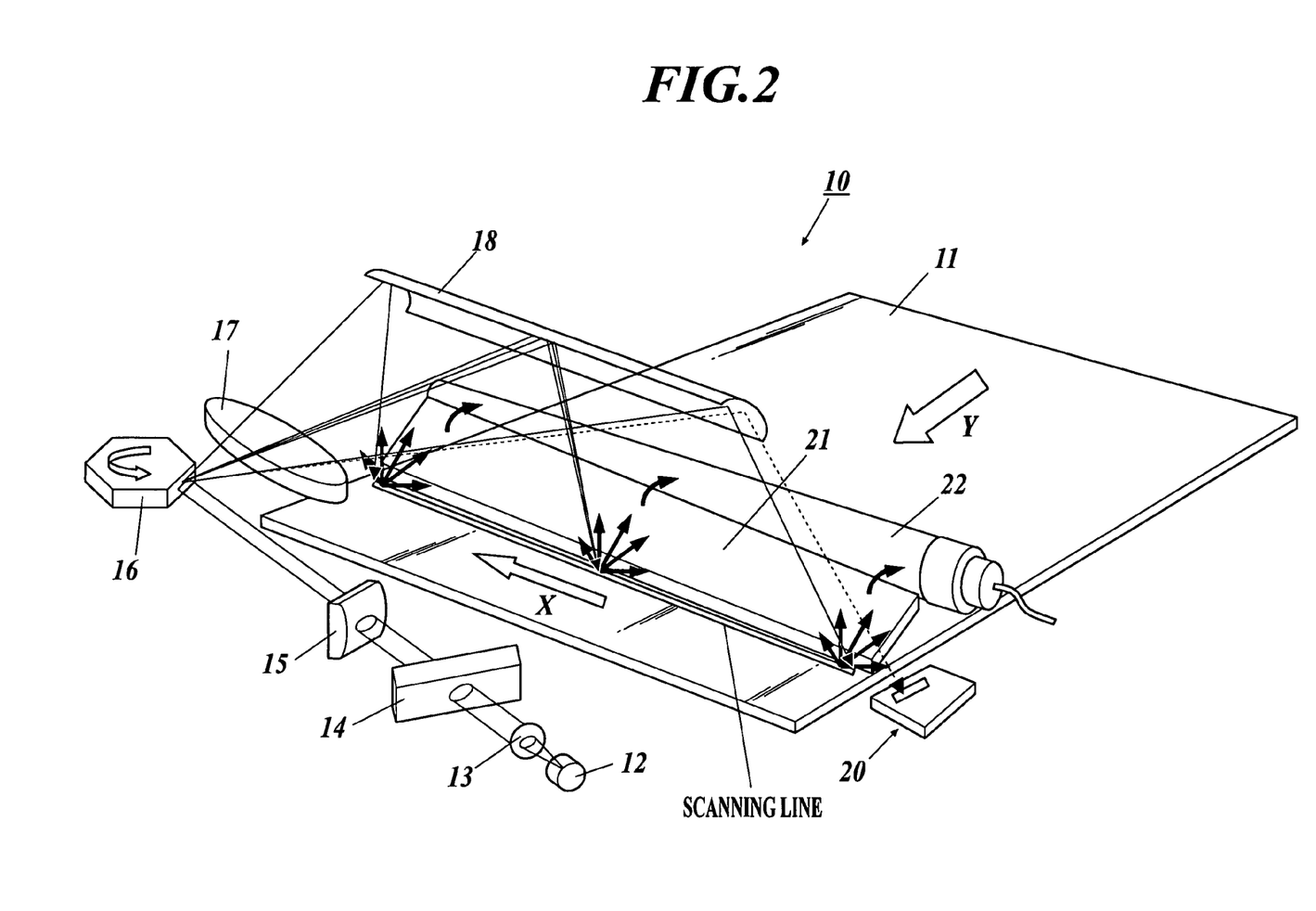
FIG. 2 is a rough perspective view showing a radiation detector relating to the first embodiment.

Here, in the present first embodiment, a CR 10 shown in FIG. 2 is applied as the radiation detector 4.

As shown in FIG. 2, the CR 10 comprises a photostimulable phosphor plate 11 structured from a generally-known photostimulable phosphor, and a semiconductor laser 12 for emitting an stimulating light (laser light) to be irradiated to the photostimulable phosphor plate 11. In the traveling direction of the laser light emitted from the semiconductor laser 12, a collimate lens 13, a beam splitter 14, a cylindrical lens 15 and a polygon mirror 16 are arranged in this order. An fθ lens 17 and a cylindrical lens 18 are placed from the polygon mirror 16 to above the photostimulable phosphor plate 11.

In the CR 10, when the semiconductor laser 12 emits the laser light, the laser light is changed to a collimated light by the collimate lens 13 and enters the beam splitter 14. Thereafter, the light goes through the beam splitter 14 and the cylindrical lens 15 and enters the polygon mirror 16 to be reflected at the polygon mirror 16. The polygon mirror 16 rotates in a counterclockwise direction in FIG. 2. The laser light reflected at the polygon mirror 16 goes through the fθ lens 17 and reflected at the cylindrical lens 18. Then, the laser light scans over the photostimulable phosphor plate 11 along a scanning direction X in FIG. 2 in conjunction with the rotation of the polygon mirror 16.

Beside the photostimulable phosphor plate 11, a horizontal synchronization (H-SYNC) sensor 20 for detecting the laser light emitted from the semiconductor laser 12 is placed. The H-SYNC laser 20 is placed on the scanning line of the laser light (on an extended line of the main-scanning direction X). Before the scanning by the laser light over the photostimulable phosphor plate 11, the H-SYNC sensor 20 detects the laser light prior to the scanning and generates a synchronization signal to start the scanning.

Above the photostimulable phosphor plate 11, a condenser 21 having a flat plate shape and a photomultiplier 22 having a cylindrical shape are provided. The condenser 21 has approximately the same width as that of the photostimulable phosphor plate 11, and the condenser 21 guides a photostimulable light (photostimulably emitted light) emitted from the photostimulable phosphor plate to the photomultiplier 22. The photomultiplier 22 detects the light guided by the condenser 21 and photoelectrically converts the detected light. The photomultiplier 22 is placed along the scanning direction X of the laser light, sequentially detects the light emitted from the photostimulable phosphor plate 11 along the scanning direction X, and generates an electrical signal corresponding to the light intensity distribution along the scanning line of the laser light.

Here, in the CR 10, a conveyance mechanism (illustration omitted) for conveying the photostimulable phosphor plate 11 in a cross scanning direction Y, which is approximately perpendicular to the scanning direction X, is placed. At each time of the laser scanning, the conveyance mechanism is actuated for intermittently conveying the photostimulable phosphor plate 11 in the cross scanning direction Y.

Continuously, an operation of the radiation image reading system 1 relating to the first embodiment will be described.

When a radiography of the subject 3 is started, the radiation source 2 irradiates a radiation toward the subject 3, and the radiation transmitted through the subject 3 enters the photostimulable phosphor plate 11 of the CR 10 and the photostimulable phosphor plate 11 accumulates the radiation.

After the radiography of the subject 3 is completed, in the CR 10, the semiconductor laser 12 emits the laser light, and the laser light is transmitted through the optical system, which is from the collimate lens 13 to the cylindrical lens 18. Through the transmittance, first, the laser light enters the H-SYNC sensor 20 for generating the synchronization signal to start the scanning, and thereafter the laser light scans over the photostimulable phosphor plate 11 along the scanning direction X (on the scanning line) in conjunction with the rotation of the polygon mirror 16.

During the scanning of the laser light, when the laser light enters the photostimulable phosphor plate 11, a photostimulable phosphor of the entering position is excited and emits a photostimulable light, and the light is guided to the photomultiplier 22 by the condenser 21 and an electrical signal (analog signal) corresponding to the scanning is generated in the photomultiplier 22.

When one time of the scanning of the laser light along the scanning direction X is completed, the photostimulable phosphor plate 11 is intermittently conveyed as much as predetermined amount along the cross scanning direction Y, and the scanning of the laser light that is the same as the above-mentioned scanning is re-performed. Thereafter, in the CR 10, the intermittent conveyance of the photostimulable phosphor plate 11 and the scanning of the laser light are repeatedly performed, and at each time of the scanning of the laser light, an image signal (analog signal) corresponding to a dose of the radiation accumulated in the photostimulable phosphor plate 11 is generated.

Thereafter, the analog signal generated in the CR 10 as the radiation detector 4, is inputted from the radiation detector 4 to the A/D converter 5.

The A/D converter 5 is a core for digitizing the analog signal, and performs two principal processes which are "sampling" and "quantization", respectively. The first embodiment has a specific technical feature in regard to the above-mentioned sampling. Hereinafter, the sampling will be described in detail.

Figure 3A:
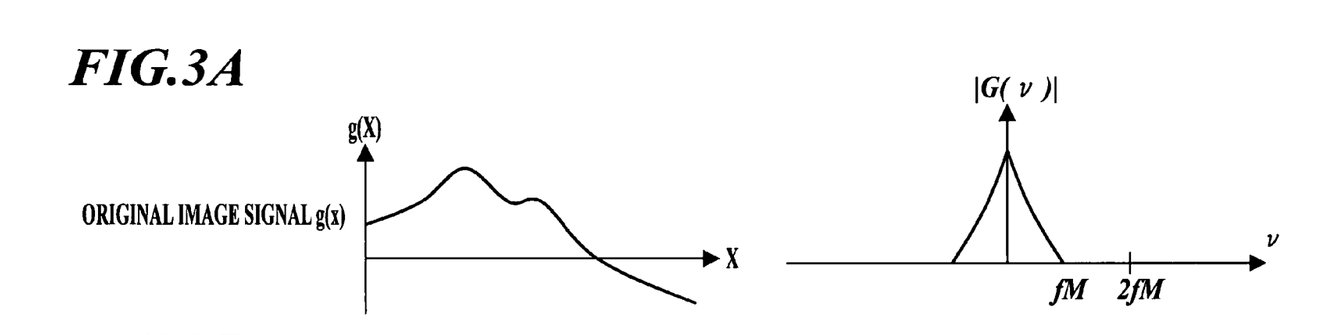
FIGS. 3A to 3C are views for describing a sampling principle.
Figure 3B:
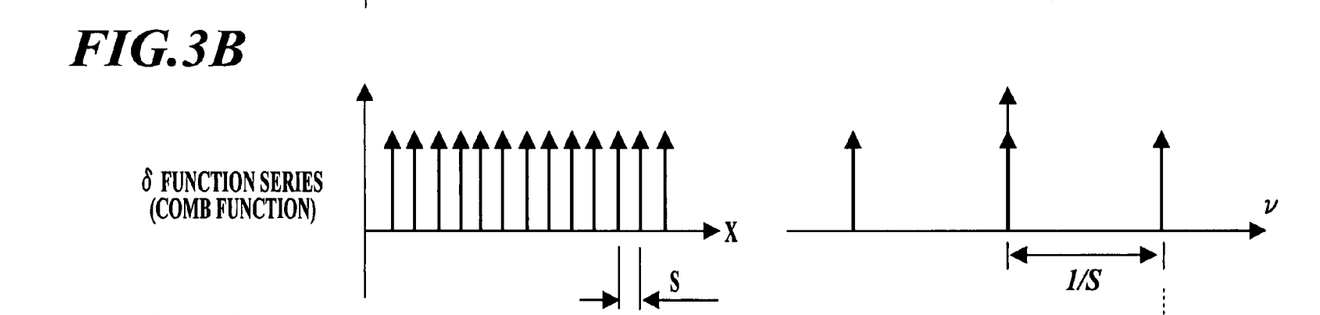
Figure 3C:
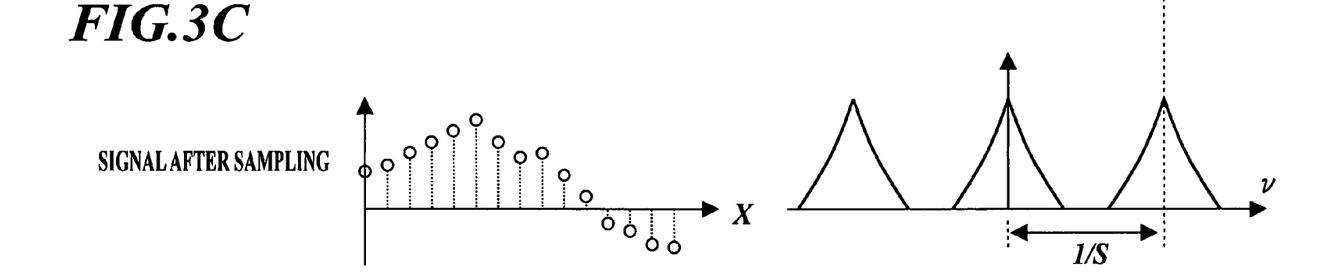

The A/D converter 5 as a sampling section samples the image signal (analog signal) inputted from the CR 10 as the radiation detector 4. According to the sampling principle, the aliasing occurs unless the sampling is performed by a sampling frequency being larger than a frequency two times as much as the frequency of the image signal before the sampling. In other words, as shown in FIGS. 3A to 3C, under the assumption that the image signal before the sampling has a spatial frequency of maximum $f_M$, since "sampling" is performed by a calculation of multiplying $\delta$ function series (hereafter, it is referred to as "comb function"), in a frequency area, a calculation of convoluting a Fourier transform of the comb function over the frequency components of the original image signal (convolution integral) is performed. Since the Fourier transform of a comb function results in a comb function after all, when a sampling interval is set to S, ultimately, a duplication having the same shape as the frequency components of the original image signal is generated at each sampling frequency Vs=1/S.

Figure 4A:
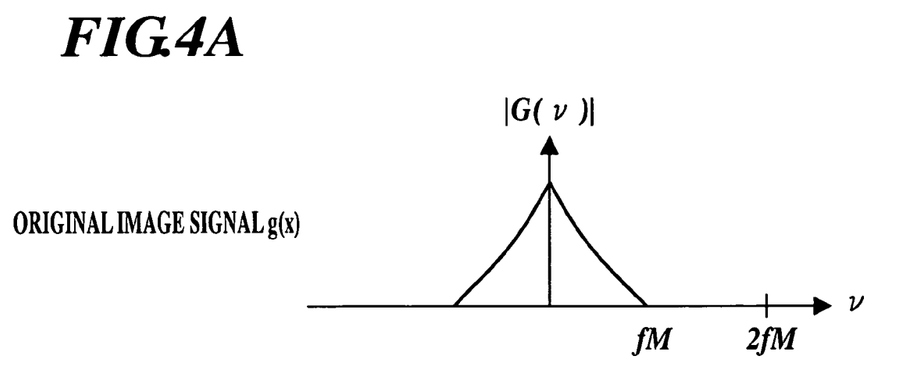
FIGS. 4A and 4B are views for describing an aliasing.
Figure 4B:
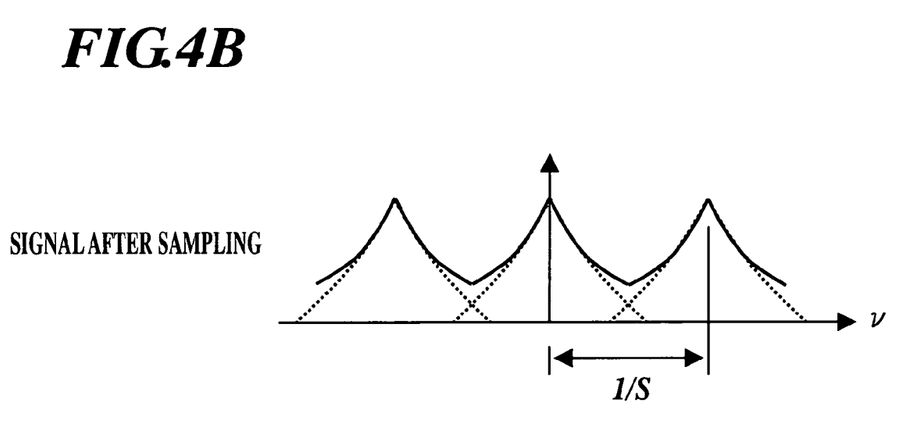

On the other hand, as shown in FIGS. 4A and 4B, when the sampling frequency is smaller than $2f_M$, feet of adjacent duplications overlap each other and are summed, and thereby the phenomenon of "aliasing" occurs. When "aliasing" occurs, a noise component increases and a false signal is generated, and therefore it is not preferable.

Here, a focus blur in a magnified image generation will be described.

Figure 5:
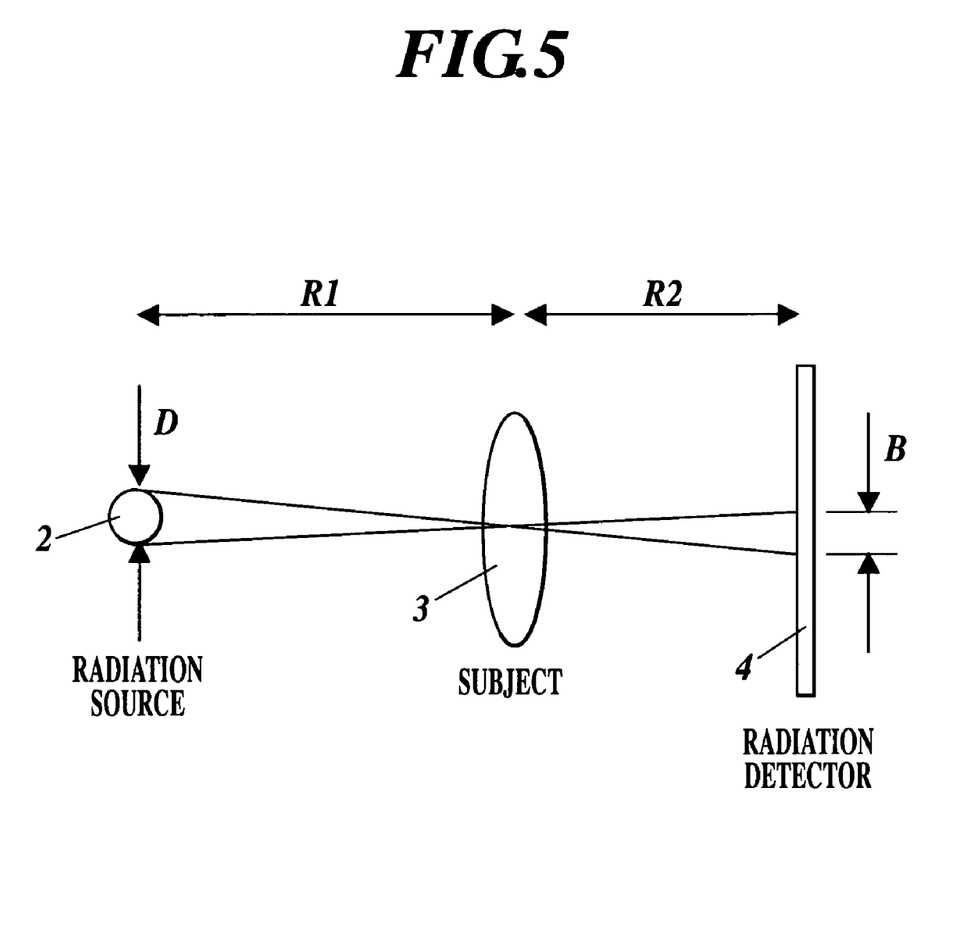
FIG. 5 is a view for describing a focus blur upon a magnified image generation.

As shown in FIG. 5, because of a geometrical unsharpness on the radiation detector 4, a cast image of the subject 3 gets blurred. The geometrical unsharpness is called as "penumbra", and a size thereof B is simply given as the following geometrical relation:

$$B = D \times (R2/R1) \quad (1)$$

where D is a size of the radiation source. For the ease of descriptions, under the assumption that things are considered one-dimensionally and an intensity distribution of the radiation source 2 is uniform at the inside of the radiation source and is zero at the outside, the intensity distribution of the radiation source 2 becomes a rectangular function having a width of D, and a penumbra becomes also a rectangular function having a width of B. This penumbra becomes a factor of deteriorating a sharpness of the image as a blurring function or a Line Spread Function (LSF).

Here, according to FIG. 5, a magnification ratio M at a magnified radiography is given as the following equation (2):

$$M = 1 + R2/R1 \quad (2)$$

In the first embodiment, in order to obtain a sufficient magnification effect in the magnified radiography, preferably the magnification ratio M should satisfy the following condition (3):

$$M \geq 1.2 \quad (3)$$

Then, in consideration of a Modulation Transfer Function (MTF) to which the above-mentioned penumbra is evaluated, in the first embodiment, an MTF of the radiation detector 4 to which a Fourier transform of the LSF according to the penumbra is evaluated becomes a comprehensive MTF.

Figure 6:
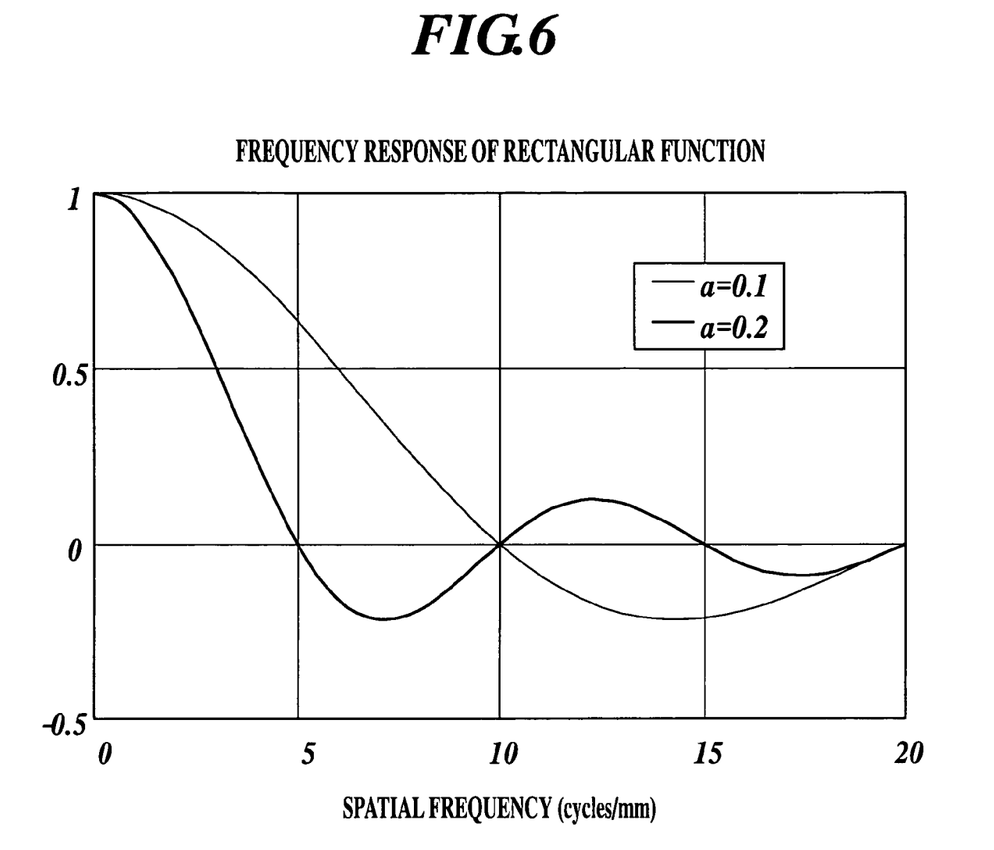
FIG. 6 is a view showing a frequency response with respect to a spatial frequency of a rectangular function.

A Fourier transform of a rectangular function becomes, as well known, a sinc function. In other words, with a rectangular function having a width of a and a height of 1 defined as rect(x/a), and a Fourier transform thereof is given as:

$$F\{rect(x/a)\} = a \times sinc(av)$$

and when a normalization is performed so as to make $v \to 0$, it is given as:

$$FN\{rect(x/a)\} = F\{rect(x/a)\}/a = sinc(av) = sinc(a\pi v)/(a\pi v).$$

Therefore, as shown in FIG. 6, this function has a zero point at each frequency of 1/a, and the function changes its sign at each frequency of 1/a.

Here, in the first embodiment, by paying attention to the fact that a zero point exists in a frequency response of the penumbra in the magnified radiography, the frequency response of the penumbra is used as an anti-aliasing filter in the cross scanning direction Y. In other words, the Nyquist frequency $v_N$ for the sampling is made approximately equal to the frequency of the zero point of the penumbra. Thereby, the penumbra plays a roll of the anti-aliasing filter, whereby it is possible to prevent the aliasing.

In reality, by setting the frequency of the zero point to $V_0 = 1/B$, when the Nyquist frequency $v_N$ is within a range of the following inequality (4), it is possible to obtain a similar effect.

$$0.7 v_0 \leq v_N \leq 1.3 v_0 \quad (4)$$

Figure 7:
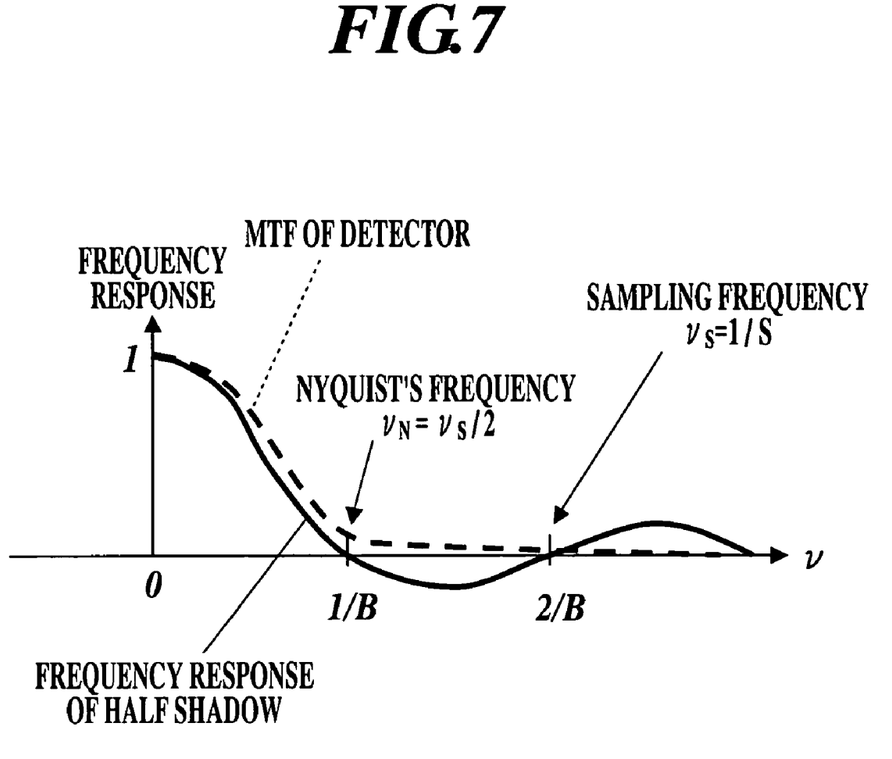
FIG. 7 is a view showing an MTF of the radiation detector and a frequency response of a penumbra with respect to a spatial frequency when a frequency of a zero point is equal to a Nyquist frequency.

As one example of the condition of the above-mentioned inequality (4), FIG. 7 shows a pattern diagram showing a case of $v_0 = v_N$.

When the above-mentioned inequity (4) is given by a size B of the penumbra and a sampling interval S, the following inequality (4.1) is given:

$$1.4S \leq B \leq 2.6S \quad (4.1)$$

For example, when the sampling interval is set to S=0.044 (mm), according to the above-mentioned condition (4.1), the size B of the penumbra should be set to $0.062 \leq B \leq 0.114$.

Further, when the condition of the above-mentioned inequality (4.1) is described in regard to the sampling interval S, the following inequality (4.2) is given.

$$B/2.6 \leq S \leq 1.4 \quad (4.2)$$

For example, when the size of the penumbra is set to B=0.3 (mm), according to the condition of the above-mentioned (4.2), the sampling interval S (mm) should be set to $0.115 \leq S \leq 0.214$.

Based on the above-mentioned principles, in the first embodiment, the A/D converter 5 samples the analog signal and quantizes the analog signal after the sampling, whereby the image signal inputted from the radiation detector 4 is converted into the digital signal.

Here, upon the sampling of the analog signal by the A/D converter 5, when a pre-sampling MTF at the spatial frequency v of the CR 10 as the radiation detector 4 is set to MTFp(v) and the Nyquist frequency is set to $v_N$, when $v \geq v_N$, preferably MTFp(v)$\leq$0.1 is satisfied. Thereby, it is possible to reduce the frequency component of $v \geq v_N$ of the signal prior to the A/D conversion, and even when the folding exists, it is possible to reduce an influence thereof at the minimum extent.

Thereafter, the digital signal generated by the A/D converter 5 is inputted from the A/D converter 5 to the computer 6.

The computer 6 comprises a processor such as a CPU (Computer Processing Unit) or the like. By an execution process of the processor according to operator's instruction, the inputted digital signal is stored in the storing device 7 as digital data, or the inputted digital signal is converted into an analog signal by the D/A converter 8 to be displayed on the display device 9 as a radiation image of the subject 3.

Second Embodiment

Figure 8:
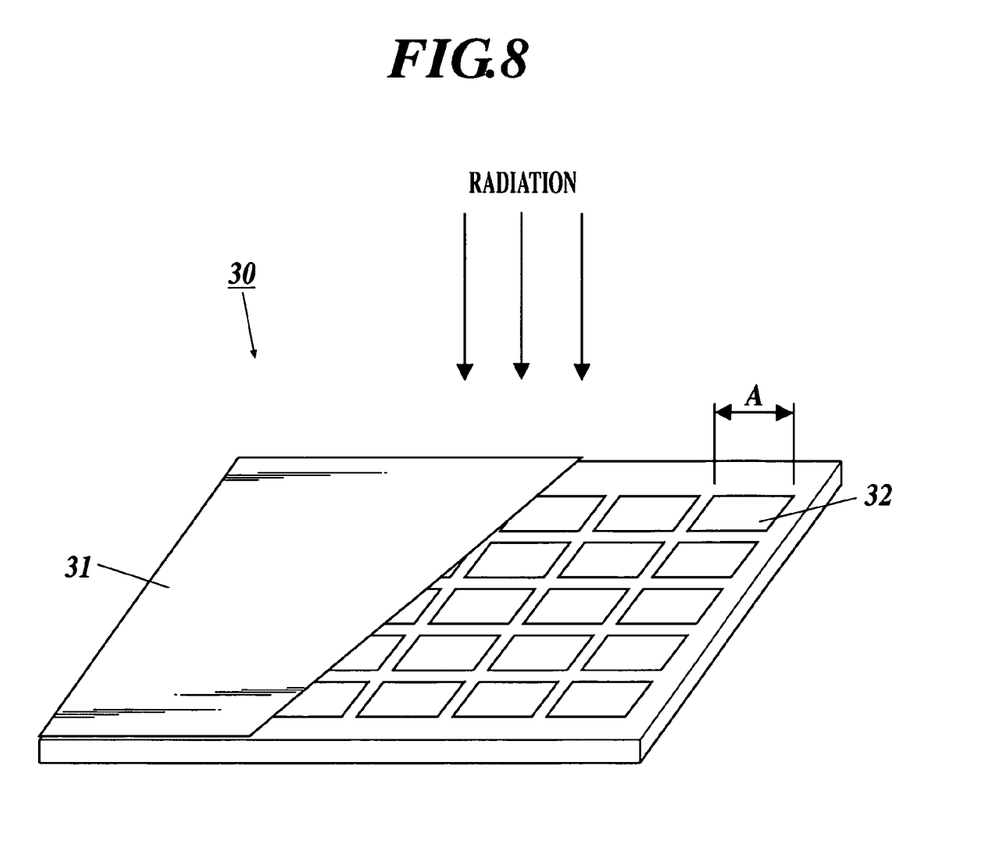
FIG. 8 is a rough perspective view showing the radiation detector relating to the second embodiment.

A radiation image reading system relating to the present second embodiment is the same as the radiation image reading system 1 relating to the first embodiment in view of structures and operations, except that in the second embodiment, an FPD 30 shown in FIG. 3 is applied as the radiation detector 4 of the radiation image reading system 1 relating to the first embodiment, and a configuration of the sampling in the A/D converter 5 is different from that of the first embodiment.

The FPD 30 shown in FIG. 8 is an example of a plane detector by one-dimensional or two-dimensional array of micro detectors having a predetermined aperture. The FPD 30 comprises a known scintillator 31 for emitting a fluorescence by irradiating a radiation, and large number of photo detectors 32, 32, . . . such as a photodiode for receiving the fluorescent having amount corresponding to its intensity. The photo detectors 32 are so arranged in a matrix form as to have a minute interval from each other. To each photo detector 32, a scanning line that is connected to a scanning driver and a signal line that is connected to a signal driver are connected (illustration omitted).

Here, an area at which each photo detector is capable of detecting the fluorescence is called "aperture", and in the second embodiment, a size of the aperture of each photo detector 32 is set to A.

In the second embodiment, when a radiography of the subject 3 is started, the radiation source 2 irradiates a radiation toward the subject 3, and the radiation transmitted through the subject 3 enters the scintillator 31 of the FPD 30. The scintillator 31 emits a fluorescent corresponding to dose of the entered radiation, and each photo detector 32 receives the fluorescent.

Thereafter, in the FPD 30, a signal indicating a scanning start is supplied to each scanning line by the scanning driver, and an electrical signal corresponding to an intensity of the received fluorescence (radiation dose transmitted through the subject 3) is supplied from the photo detectors 32, 32, . . . connected to the scanning line to the signal driver through the signal line. Then, the signal driver outputs the electrical signal to the A/D converter 5 as an image signal (analog signal), and the image signal is inputted to the A/D converter 5.

The A/D converter 5, as a sampling section, performs the sampling to the inputted image signal. However, when the FPD 30 is applied as the radiation detector 4, the sampling principle is different from that of the above-mentioned first embodiment, and a sinc function corresponding to a rectangular function having a width of A which is equal to the size of the aperture of each photo detector 32 is multiplied to an MTF in a frequency area. In general, since the size A of the aperture is approximately equal to a pixel size, that is the sampling interval S, a vicinity of the first zero point of the sinc function of the aperture automatically becomes the Nyquist frequency $v_N$.

However, when the FPD 30 is applied as the radiation detector 4, generally a sharpness of the detector is high, and therefore the pre-sampling MTF has a sufficiently high value even in a case of not less than the Nyquist frequency $v_N$. Therefore, there is a circumstance in which it is not possible to ignore the folding of a minus part after the first zero point.

Figure 9:
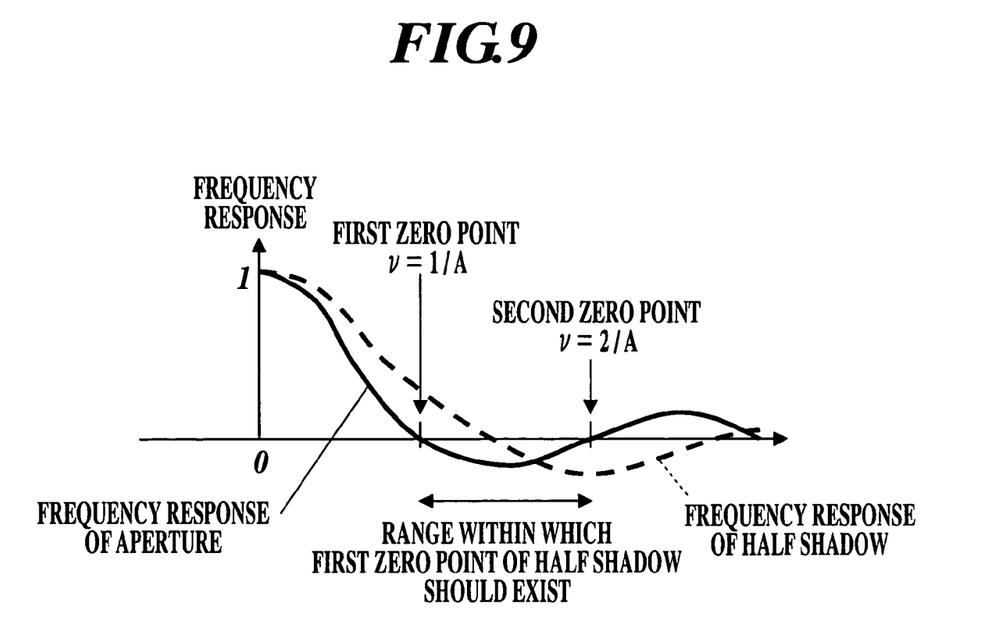
FIG. 9 is a view showing a frequency response of an aperture and a frequency response of a penumbra with respect to a spatial frequency.

Here, in the case of the magnified radiography, in consideration of the fact that the sinc function of the penumbra is always multiplied to the original image signal prior to the sampling, even when the FPD 30 is applied as the radiation detector 4, an optimal sampling frequency exists. In other words, as shown in FIG. 9, when a size of the penumbra is set to B, if a position of the first zero point 1/B by the penumbra exists between the first zero point 1/A by the sinc function of the aperture and the second zero point 2/A, a minus part of the sinc function of the aperture is reduced to an ignorable level, and thereby it is possible to prevent the aliasing.

When this is described by a relational expression, with a size of the aperture set to A, the following inequity (5) should be satisfied:

$$1/A \leq 1/B \leq 2/A \text{ (or } A/2 \leq B \leq A) \ldots \quad (5)$$

For example, when a size of each photo detector 32 is set to A=100 μm, according to the above-mentioned condition (5), the size B (μm) of the penumbra should satisfy $50 \leq B \leq 100$.

Conversely, when a range of the size A of the aperture is set with respect to the size B of the penumbra, the above-mentioned condition (5) is given as the following inequity (5.1).

$$B \leq A \leq 2B \ldots \quad (5.1)$$

For example, when a size of the penumbra is set to 75 μm, according to the above-mentioned condition (5.1), the size A (μm) of the aperture should satisfy $75 \leq B \leq 150$.

The above-mentioned inequity is described as the following inequity (5.2) under the assumption that the size A of the aperture is equal to a pixel size, that is, the sampling interval S. When it is not possible to accurately specify a size A of the aperture of each photo detector 32, it is possible to assume A=S.

$$B \leq S \leq 2B \ldots \quad (5.2)$$

Figure 10:
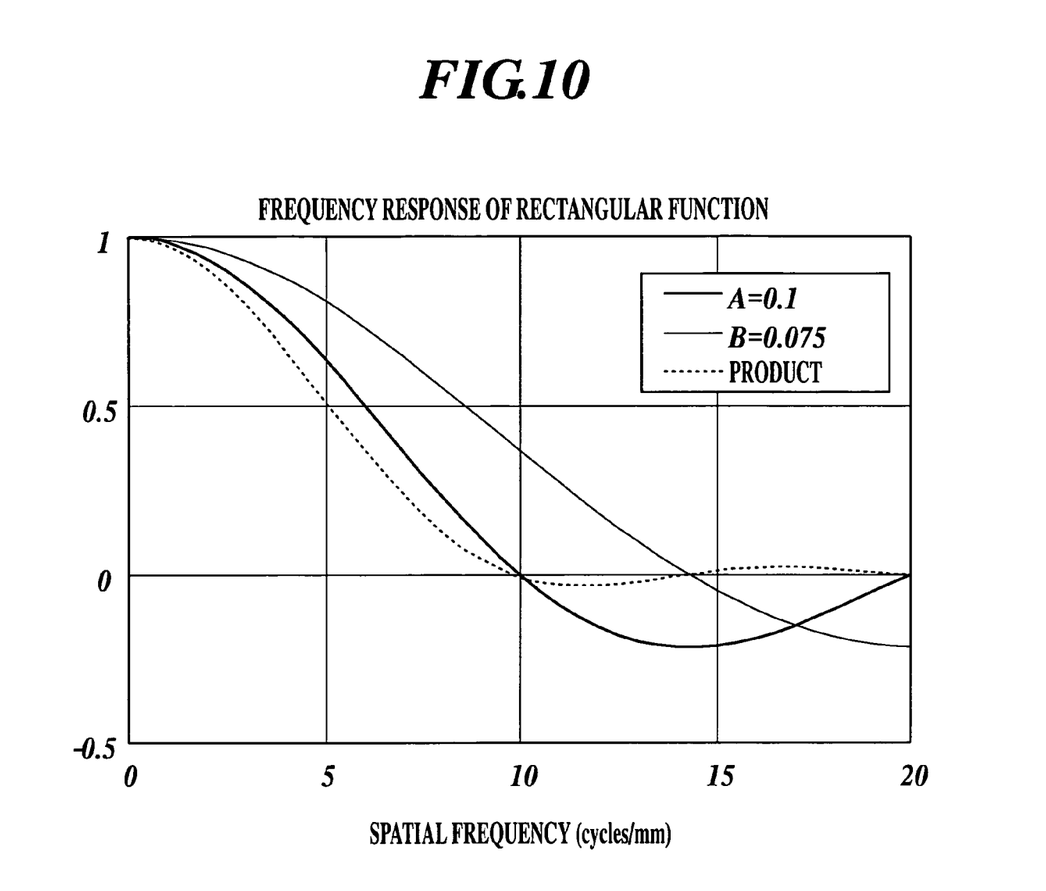
FIG. 10 is a view showing a frequency response with respect to a spatial frequency of a rectangular function.

FIG. 10 shows a frequency response when A=0.1 mm (100 μm) and B=0.075 mm (75 μm), with the FPD 30 applied as the radiation detector 4. In this case, the first zero point of the rectangular function of the penumbra exists around the center between the first zero point and the second zero point of the rectangular function of the aperture of each photo detector 32 (circled portion in FIG. 10). As a result, the product is approximately zero after the first zero point of the aperture, and thereby it is possible to recognize that an influence of the aliasing has been eliminated.

Here, in the second embodiment as well as the above-mentioned first embodiment, a magnification ratio M at the magnified radiography is given as the above-mentioned equation (2), and in order to obtain a sufficient magnification effect at the magnified radiography, the magnification ratio M should satisfy the above-mentioned condition (3).

In accordance with the above-mentioned principles, the A/D converter 5 samples the image signal inputted from the FPD 30 as the radiation detector 4, and quantizes the image signal following the sampling.

EXAMPLE 1

In the example 1, by using a product similar to the radiation detector (CR) shown in FIG. 2 (used plate is a REGIUS plate RP-3S manufactured by Konica Minolta Medical & Graphic, Inc.), with a size of the penumbra set to B=0.3 mm, a lead chart was radiographed when the inequities (4.1) and (4.2) in the above-mentioned first embodiment were satisfied and when the inequities (4.1) and (4.2) were not satisfied, and whether a spurious resolution was generated or not according to the aliasing was examined. The result is shown in the following Table 1. In the Table 1, "○" indicates resolving, "—" indicates not resolving, and "×" indicates a spurious resolution. Here, the chart frequency is a value on the radiation detector.

TABLE 1

| SAMPLING INTERVAL IN CROSS SCANNING DIRECTION (mm) | CHART FREQUENCY (lp/mm) | | | | | | | |
|---|---|---|---|---|---|---|---|---|
|  | 1 | 1.5 | 2 | 2.5 | 3 | 4 | 5 | ETC |
| 0.0875 | ○ | ○ | ○ | — | — | × | × | COMPARISON |
| 0.175 | ○ | ○ | ○ | ○ | — | — | — | PRESENT INVENTION |

As shown in Table 1, when the conditions of the inequities (4.1) and (4.2) of the above-mentioned first embodiment were satisfied, a spurious resolution was not generated, and thereby it was possible to obtain an accurate image. Here, in regard to the chart frequency of not less than 6 l p/mm, corresponding results are omitted as all of them did not resolve.

EXAMPLE 2

In the present example 2, by using a product similar to the radiation detector (FPD) shown in FIG. 8 (size of the aperture is A=0.1 mm), a lead chart was radiographed when the inequity (5) in the above-mentioned second embodiment was satisfied (when a size of the penumbra is set B=0.075 mm) and when the inequity (5) was not satisfied (when a size of the penumbra is set B=0.15 mm), and whether a spurious resolution was generated or not according to the aliasing was examined. The result is shown in the following Table 2. In the Table 2, "○" indicates resolving, "—" indicates not resolving, and "×" indicates a spurious resolution. Here, the chart frequency is a value on the radiation detector.

TABLE 2

| SIZE OF PENUMBRA (mm) | CHART FREQUENCY (lp/mm) | | | | | | | |
|---|---|---|---|---|---|---|---|---|
|  | 3 | 5 | 6 | 7 | 8 | 9 | 10 | ETC |
| 0.0875 | ○ | ○ | ○ | ○ | ○ | — | — | COMPARISON |
| 0.175 | ○ | ○ | ○ | × | × | — | — | PRESENT INVENTION |

As shown in Table 2, when the condition of the inequity (5) of the above-mentioned second embodiment was satisfied, a spurious resolution was not generated, and thereby it was possible to obtain an accurate image.

The entire disclosure of a Japanese Patent Application No. Tokugan 2004-171282 filed on Jun. 9, 2004, including specifications, claims, drawings and summaries are incorporated herein by reference in their entirety.

What is claimed is:

1. A radiation image reading system comprising:
   a radiation source for irradiating a radiation toward a subject, the radiation source having a size D;
   a radiation detector in which large number of detecting devices for detecting the radiation transmitted through the subject are arranged in an array form, for generating an image signal of the subject by detecting the radiation transmitted through the subject by each of the detecting devices, an aperture of each of the detecting devices having a size A; and
   a sampling section for sampling the image signal
   wherein the size A of the aperture fulfills a condition of B≦A≦2B, where B is a size of a penumbra on the radiation detector, and
   the size B of the penumbra is represented by B=D× (R2/R1), where R1 is a distance from the radiation source to the subject and R2 is a distance from the subject to the radiation detector.

2. The system of claim 1, wherein a magnification ratio M satisfies a condition of M=1+R2/R1≧1.2.

3. The system of claim 1, wherein the radiation detector is a flat panel detector comprising a scintillator, and the detecting devices are photo detectors to detect fluorescence emitted from the scintillator.

* * * * *